United States Patent

Maldonado et al.

[11] 4,422,856
[45] Dec. 27, 1983

[54] N-SUBSTITUTED SUCCINIMIDES, THEIR PREPARATION AND USE AS MOTOR FUEL ADDITIVES

[75] Inventors: Paul Maldonado, Saint Symphorien d'Ozon; Choua Cohen; Bernard Sillion, both of Lyons, all of France

[73] Assignees: Institut Francais du Petrole, Rueil-Malmaison; Elf-France, Paris, both of France

[21] Appl. No.: 234,134

[22] Filed: Feb. 13, 1981

[30] Foreign Application Priority Data

Feb. 15, 1980 [FR] France ................................ 80 03459

[51] Int. Cl.$^3$ ................................................ C10L 1/22
[52] U.S. Cl. ...................... 44/63; 44/71; 252/51.5 A; 548/544; 548/546; 548/547
[58] Field of Search ................ 44/63, 71; 252/51.5 A; 260/326.5; 548/544, 546, 547

[56] References Cited

U.S. PATENT DOCUMENTS

| | | | |
|---|---|---|---|
| 2,977,309 | 3/1961 | Godfrey et al. | 252/51.5 A |
| 3,184,474 | 5/1965 | Catto et al. | 252/51.5 A |
| 3,576,743 | 4/1971 | Widmer et al. | 252/51.5 A |
| 3,632,511 | 1/1972 | Liao | 260/326.5 F |
| 3,897,454 | 7/1975 | Hankins et al. | 548/544 |
| 3,936,480 | 2/1976 | Demoures et al. | 44/71 |
| 3,950,341 | 4/1976 | Okamoto et al. | 252/51.5 A |

*Primary Examiner*—Jacqueline V. Howard

*Attorney, Agent, or Firm*—Millen & White

[57] ABSTRACT

N-substituted succinimides are obtained by reacting in a first stage, maleic anhydride with an oxyalkylated or polyoxyalkylated monoalcohol of formula

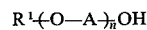
$$R^1(O-A)_nOH$$

wherein $R^1$ is an aliphatic radical having from 12 to 25 carbon atoms, A is an alkylene radical having 2 to 4 carbon atoms and n is an integer from 1 to 50, and by further reacting the reaction product of the first stage either with a monoprimary amine of formula

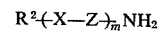
$$R^2(X-Z)_mNH_2$$

or a bi-primary amine of the formula

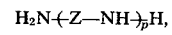
$$H_2N(Z-NH)_pH,$$

wherein $R^2$ is an aliphatic radical having from 8 to 25 carbon atoms, Z is an alkylene radical having from 2 to 4 carbon atoms, X is —NH— or —O—, m is an integer from 0 to 4 and p an integer from 2 to 6.

The resultant succinimides are useful as anti-rust and detergent additives for motor fuels.

13 Claims, No Drawings

N-SUBSTITUTED SUCCINIMIDES, THEIR PREPARATION AND USE AS MOTOR FUEL ADDITIVES

BACKGROUND OF THE INVENTION

This invention concerns N-substituted succinimides, their manufacture and use as additives for gasoline and the resultant improved gasoline compositions having good anti-rust and detergent properties in the carburetor or in the intake systems.

Erratic idling and stalling of the combustion engines operating with a carburetor are well known as difficulties associated with the driving of motor cars.

One of the reasons of the erratic idling and of the stalling of the engine is the accumulation of deposits on the throttle valve of the carburetor and on the surrounding walls.

The accumulation of deposits impedes the normal flow of air through the carburetor and consequently results in the formation of rich fuel mixtures. The deposits may be formed, for example, by accumulation of impurities or dusts from air or from the recycle gas from the engine housing.

Moreover, these mixtures of very high fuel content burn incompletely and accordingly increase the air pollution by discharging thereinto an increased proportion of partly burnt fuel particles.

The modern carburetors of large capacity have a complex structure. Even small amounts of deposits and residues, when present in the fine control members of these carburetors highly disturb the operation of the latter and result, in particular, in a bad composition of the fuel/air mixture for which the ratio $CO/CO_2$ increases.

In order to obviate these disadvantages it is necessary either to proceed periodically to an expensive cleaning of the carburetor and of the intake valve heads, or to increase the normal idling running speed with the consequence of a more difficult driving of the vehicle and a useless increase in the fuel consumption.

It is known to reduce or to prevent the accumulation of these deposits in the carburetor by making use of fuels containing additives called detergents for carburetors.

In addition to these detergent additives for carburetors, the modern fuels require further additives for improving the behaviour of the fuel, such as anti-rust additives and additives for reducing the deposits in the admission system. Preferably multifunctional additives are used.

Although many multifunctional additives have been proposed in this technical field, many of them are not acceptable as a consequence either of undesirable effects of their use or of the excessive amount of additive required for obtaining the desired properties.

OBJECTS OF THE INVENTION

It is an object of the present invention to provide a family of additives exhibiting multifunctional properties, including anti-rust and detergent properties in the carburetor and which do not produce undesirable deposits on the valves, when used in a proportion usually ranging from 0.001 to 0.05% by weight with respect to the weight of the hydrocarbon mixture, although these limits are not compulsory.

DETAILED DISCUSSION

More generally, the products of the invention can be defined as those obtained by reacting maleic anhydride with at least one oxyalkylated or poly-oxyalkylated monoalcohol of the general formula:

$$R^1\text{-}(O\text{-}A)_n\text{OH} \qquad (I)$$

wherein $R^1$ is a linear or branched saturated or unsaturated aliphatic radical containing from 12 to 25 carbon atoms, preferably from 12 to 22 carbon atoms, A is a linear or branched alkylene radical containing from 2 to 4 carbon atoms, at least two of which are in a straight chain and n is an integer from 1 to 50.

The resulting product is reacted with a monoprimary amine of the formula:

$$R^2\text{-}(X\text{-}Z)_m\text{NH}_2 \qquad (II)$$

wherein $R^2$ is a linear or branched, saturated or unsaturated aliphatic radical containing from 8 to 25, preferably from 8 to 22 carbon atoms, Z is a linear or branched alkylene radical containing from 2 to 4 carbon atoms, at least two of which are in a straight chain, X is either a —NH— group or an oxygen atom —O—, and m is an integer from 0 to 4.

Alternatively the product of the first reaction may be reacted with a bi-primary amine of the general formula:

$$H_2N\text{-}(Z\text{-}NH)_p H \qquad (III)$$

wherein Z is defined as above and p is an integer from 2 to 6.

The product resulting from the reaction of maleic anhydride with an oxyalkylated or poly-oxyalkylated monoalcohol of formula (I) may be considered as having a formula of the type:

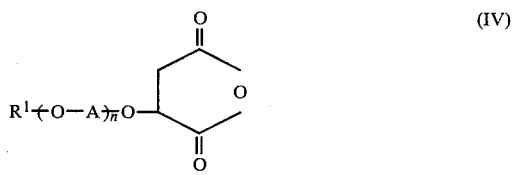

wherein $R^1$, A and n are defined as above.

In the case of use of a monoprimary amine of formula (II) in a proportion of about 1 mole per mole of anhydride of formula (IV), the final product has a formula of the type:

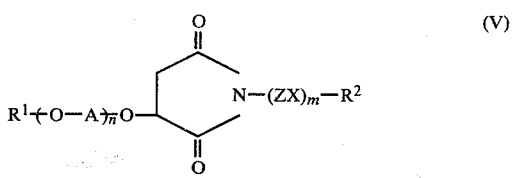

wherein $R^1$, $R^2$, A, Z, X, m and n are defined as above.

On the other hand, in the case of use of a bi-primary amine of formula (III) in a proportion of about 1 mole per 2 moles of anhydride of formula (IV), the final product may be considered as having a formula of the type:

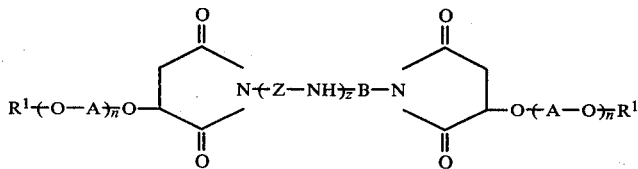

(VI)

wherein the letters have the same meaning as above defined and z is an integer equal to p−1.

In the oxyalkylated or poly-oxyalkylated monoalcohols of formula (I) used for the preparation of the anhydrides of formula (IV), the radical $R^1$ is preferably a linear alkyl radical containing 12 or 13 carbon atoms. Moreover, these products advantageously have their terminal hydroxy group on a secondary or tertiary carbon atom of an alkylene group: the chains of recurrent alkylene units advantageously comprise a terminal propylene oxide group:

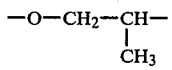

or an isobutylene oxide group:

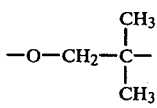

Among the oxyalkylated or poly-oxyalkylated monoalcohols of formula (I) contemplated according to the invention, the more advantageous ones include:
  polyoxypropylated lauric alcohol containing, for example, 21 propylene oxide recurrent units,
  trioxypropylated tridecyl alcohol,
  tridecyl alcohol with sequential ethylene oxide and propylene oxide recurrent units,
  tridecyl alcohol with sequential ethylene oxide and isobutylene oxide recurrent units.

Among the amines of formula (II) which can be used to prepare the products of the type of formula (V), advantageous examples are:
N-oleyl propanediamine of formula

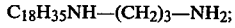

N-isotridecyl propanediamine of formula

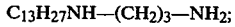

3-isotridecyloxy 1-propylamine of formula

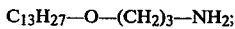

3-Hendecyloxy 1-propylamine of formula

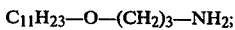

3-tridecyloxy 1-propylamine of formula $C_{13}H_{27}$—O—$(CH_2)_3$—$NH_2$; and 3-(2-ethyl hexyl) oxy 1-propylamine of formula

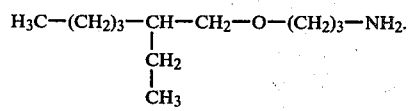

Among the amines of formula (III) which can be used for the preparation of the products of the type of formula (VI) according to the invention, the following examples are of particular advantage:
  diethylenetriamine
  tetraethylenepentamine
  dipropylenetriamine, and
  tetrapropylenepentamine.

The products of the invention can be prepared by condensation of the reactants without solvent, but preferably with a solvent, for example an aromatic hydrocarbon whose boiling point is in the range from 70° C. to 200° C., while removing the water formed during the reaction.

The reaction temperature is usually from 65° C. to 200° C., preferably from 80° C. to 160° C. The reaction lasts from 0.5 to 6 h, preferably from 1 to 3 h.

The amines of formula (II) are generally used in an amount from 1.02 to 1.2 mole and preferably from 1.05 to 1.1 mole per mole of the anhydride represented by formula (IV).

The amides of formula (III) are generally used in an amount from 1.02 to 1.2 mole and preferably from 1.05 to 1.1 mole per 2 moles of the anhydride represented by formula (IV).

The products of the invention may also be obtained by a single step of condensing maleic anhydride the oxyalkylated or polyoxyalkylated monoalcohol of formula (I) and the amine of formula (II) or the amine of formula (III).

The "ether-N-substituted succinimide" structure of the products according to the invention is ascertained by infra-red spectrometry: the infra-red spectra in fact contain succinimide absorption bands at 1700 cm$^{-1}$ and ether absorption bands at 1110 cm$^{-1}$.

These products are used as fuel additives. They offer the advantage of multifunctional properties; they have a surface-active action and exhibit good film-forming properties and improve the corrosion resistance of metal parts; in addition, their heat stability is such that they do not contribute by themselves to the formation of deposits and, as a result of their film-forming effect which is maintained at high temperature, they prevent the usual formation of deposits from lubricating oil particles or aromatic or olefinic products decomposed by heat to some extent.

The products according to the invention may be used in motor fuels at concentrations of, for example, 10 to 500 and preferably 20 to 200 parts per million (ppm) by weight, without occurrence of any trouble, even at low temperature, and they may be associated without disadvantage to other usual additives.

The following examples illustrate the invention but must not be considered to limit in any way the scope thereof.

EXAMPLE I

In a reactor of a two liter capacity, is introduced 715 g (0.5 mole) of polypropylene glycol monolauryl-ether (i.e. polyoxypropylated lauric alcohol containing about 21 propylene oxide recurrent units per molecule) which is heated under a nitrogen atmosphere and under stirring at 185° C. 53.9 g (0.55 mole) of maleic anhydride are then added thereto, and the reaction is conducted for 15 h at 185° C. under a nitrogen atmosphere.

After cooling, a yellow-orange oil is recovered, whose I.R. spectrum corresponds to the structure of a polypropoxylated succinic anhydride. 153.8 g of said oil are added to a solution of 39.6 g (0.12 mole) of N-oleyl propanediamine in 250 ml of xylene.

The mixture is heated to reflux for 3 h 30 at 144° C., with azeotropic distillation of the water formed during the reaction. There is thus obtained 378 g of a 50% solution in xylene of a product whose polypropoxylated N-alkenyl succinimide structure is ascertained by I.R. spectrometry.

EXAMPLE II 9.8 g (0.1 mole) of maleic anhydride and 145 g (0.1 mole) of polypropylene glycol mono-lauryl-ether (i.e. polyoxypropylated lauric alcohol containing about 21 propylene oxide recurrent units per molecule) are dissolved in 150 ml of xylene in a reactor.

After heating for 3 h at reflux, the mixture is cooled to room temperature and 36 g (0.1 mole) of N-oleyl propanediamine are added thereto.

The mixture is again heated for 3 h at reflux at 145° C., with azeotropic distillation of the formed water.

There is obtained a 50% solution in xylene of a product whose structure, as ascertained by I.R. spectrometry, is identical to that of the product obtained in the preceding example.

EXAMPLE III

Example I is repeated, except that a solution of 9.90 g (0.06 mole) of tetraethylenepentamine in 250 ml of xylene is added to the 153.8 g of the oil formed in the first step which constitutes the polypropoxylated succinic anhydride.

The mixture is heated to reflux for 3 h 30 at 144° C., with azeotropic distillation of the water formed during the reaction. The desired product, obtained as a 50% solution in xylene, is a triamino-bis(polypropoxylated succinimide) as ascertained by I.R. spectrometry.

TESTS PERFORMED WITH THE PRODUCTS

The products prepared as described in examples I and II have been used as additives in gasolines and the performances of the additive-containing gasolines have been determined in a number of tests hereinafter described:

(a)—Heat stability by ISD process

The ISD (Induction System Deposit) process is conducted according to the experimental method developed by the Southwest Research Institute (San Antonio—Texas) by A. A. JOHNSTON and E. DIMITROFF, SAE Transactions, Vol. 75, p. 885–891, Article 660 783 (1969).

This process provides for the estimation of the heat stability of an additive in solution in a premium gasoline by simulation of its passage on hot surfaces of a running engine and particularly on the intake valve.

The products of examples I and II have been added at a concentration of 0.01% by weight in the premium gasoline. The results are reported in Table I below. Comparative results of the premium gasoline without additive and of a premium gasoline containing the same proportion of a conventional additive are also reported.

TABLE I

| Tested products | Tests DEPOSITS ON HOT SURFACES at 200° C. in mg (tests ISD) |
|---|---|
| Premium gasoline without additive | 0 |
| Premium gasoline + compound of example I at 0.01% | 0 |
| Premium gasoline + compound of example II at 0.01% | 0 |
| Premium gasoline + conventional additive A at 0.01% | 1.8 |

(b)—Corrosion test and measurement of the interfacial tension.

The products of examples I and II have been used in a premium gasoline at a concentration of 0.01% by weight.

The corrosion test consits of determining the extent of the corrosion produced by synthetic sea water on cylindrical samples of ordinary polished steel, according to modified standard ASTM D 665 (temperature 32.2° C.; duration 20 h.).

The interfacial tension was measured according to standard ASTM D 971. The results are reported in Table II, which further indicates, by way of comparison, the results obtained with a premium gasoline without additive and those obtained with the premium gasoline containing a conventional additive at a concentration of 0.01% by weight.

TABLE II

| | Tests | |
|---|---|---|
| Tested products | CORROSION % | INTERFACIAL TENSION WATER-PREMIUM GASOLINE dynes/cm |
| Premium gasoline without additive | 100 | 38.2 |
| Premium gasoline + compound of example I at 0.01% | 0.5 | 8.2 |
| Premium gasoline + compound of example II at 0.01% | 0 | 9.4 |
| Premium gasoline + conventional additive B at 0.01% | 95 | 31.5 |

(c)—Bench test of carburetor fouling

The bench test of carburetor fouling is conducted according to the method BNPe R5 GTL developed by ELF/IFP.

This method consists of estimating on a combustion engine at bench the capacity of a motor fuel to maintain a carburetor clean.

The test is performed in 12 hours and comprises 2 periods of 6 hours separated by a stopping period of 18 hours. The fouling of the carburetor is enhanced by the recycling to intake of a portion of the exhaust gases.

A visual appraisal of the state of the carburetor body is expressed by marks from 0 to 10.

10 is the mark for a new carburetor 0 is the mark for a foul carburetor.

The mark takes into account the presence of deposits, their colour and their position in the carburetor and on the intake butterfly valve.

The products of examples I and II have been used in a proportion of 0.0167% by weight in the premium gasoline. The results are reported in Table III which further indicates, by way of comparison, the results obtained with a premium gasoline free of additive and with a premium gasoline containing a conventional additive at a concentration of 0.0276% by weight.

TABLE III

| Tested products | Running tests CARBURETOR FOULING FINAL MARK FROM 1 to 10 |
|---|---|
| Premium gasoline without additive | 3.0 |
| Premium gasoline + compound of example I at 0.0167% | 8.2 |
| Premium gasoline + compound of example II at 0.0167% | 8.6 |
| Premium gasoline + conventional additive B at 0.0276% | 7.45 |

(d)—Intake valve fouling test at bench

The intake valve fouling test at bench is performed according to the method developed by the Research and Development Department of Deutsche BP Aktiengesellschaft in Hamburg.

Its object is to determine at the test bench the capacity of the additive-containing fuels to keep the intake valves clean.

The test consists of equipping a 1.25 Opel Kadett motor with a double carburetor. In this way it is possible to simultaneously test either an additive at two different concentrations, or two different additives or an additive-containing premium gasoline comparatively with the same premium gasoline without additive.

The test simulates a sequence of driving at normal running speed and at idling conditions at 35, 50 and 80 Km per hour.

The operation program at the test bench is as follows:
30 seconds at idle at 1000 runs per minute,
1 minute at 3000 runs per minute (r.p.m.) (corresponding to 80 Km per hour),
1 minute at 1300 r.p.m. (corresponding to 35 Km per hour),
1 minute at 1850 r.p.m. (corresponding to 50 Km per hour),
Overall duration: 40 hours.

At the end of the test a mark is given to the state of the intake valve heads in terms of milligrams of deposits per valve head, which will be indicative of the quality of the additive-containing fuel as compared to the fuel alone.

The products prepared according to examples I and II have been used in a proportion of 0.0167% by weight in the premium gasoline. The results are reported in Table IV below which also indicates the results obtained with the premium gasoline without additive and those obtained with the premium gasoline containing the same proportion of 0.0167% by weight of a conventional additive.

TABLE IV

| Tested products | Motor tests FOULING OF THE INTAKE VALVES in mg of deposits per valve |
|---|---|
| Premium gasoline without additive | 233 |
| Premium gasoline + compound of example I at 0.0167% | 162 |
| Premium gasoline + compound of example II at 0.0167% | 175 |
| Premium gasoline + conventional additive A at 0.0167% | 259 |

What is claimed is:

1. The N-substituted succinimide obtained by reacting maleic anhydride with at least one oxyalkylated or polyoxyalkylated monoalcohol of the general formula $$R^1(O-A)_nOH$$

wherein $R^1$ is a linear or branched, saturated or unsaturated $C_{12-25}$ aliphatic radical; A is a linear or branched $C_{2-4}$ alkylene radical, at least two carbon atoms of which are in a straight chain; and n is an integer from 1 to 50; and reacting the resulting succinic anhydride oxyether with a monoprimary amine of the general formula $$R^2(X-Z)_mNH_2$$

wherein $R^2$ is a linear or branched, saturated or unsaturated, $C_{8-25}$ aliphatic radical; Z is a linear or branched $C_{2-4}$ alkylene radical at least two carbon atoms of which are in a straight chain; X is —NH— or —O—; and m is an integer from 0 to 4.

2. An N-substituted succinimide according to claim 1, wherein in said oxyalkylated or polyoxyalkylated monoalcohol, the radical $R^1$ is a linear $C_{12}$ or $C_{13}$ alkyl radical.

3. An N-substituted succinimide according to claim 2, wherein said oxyalkylated or polyoxyalkylated monoalcohol is polyoxypropylated lauric alcohol, trioxypropylated tridecyl alcohol, tridecyl alcohol with sequential recurrent units of ethylene oxide and propylene oxide or tridecyl alcohol with sequential recurrent units of ethylene oxide and isobutylene oxide.

4. An N-substituted succinimide according to claim 1, wherein said monoprimary amine is N-oleyl propanediamine, N-isotridecyl propanediamine, 3-isotridecyloxy 1-propylamine, 3-hendecyloxy 1-propylamine, 3-tridecyloxy 1-propylamine or 3-(2-ethyl hexyl) oxy 1-propylamine.

5. An N-substituted succinimide according to claim 1, wherein said monoprimary amine of the general formula $$R^2(X-Z)_mNH_2$$

is used in a proportion of from 1.02 mole to 1.2 mole per mole of said succinic anhydride oxyether.

6. A motor fuel composition, comprising a major proportion of at least one motor fuel and from 10 to 500 ppm by weight of at least one N-substituted succinimide according to claim 1.

7. A motor fuel composition according to claim 6, wherein the proportion of the N-substituted succinimide is from 20 to 200 ppm by weight.

8. An N-substituted succinimide having the formula

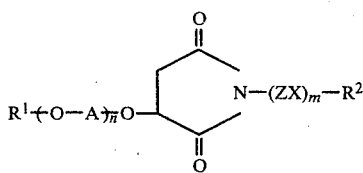

wherein $R^1$ is a linear or branched, saturated or unsaturated $C_{12-25}$ aliphatic radical; $R^2$ is a linear or branched, saturated or unsaturated, $C_{8-25}$ aliphatic radical; A is a linear or branched $C_{2-4}$ alkylene radical, at least two carbon atoms of which are in a straight chain; Z is a linear or branched $C_{2-4}$ alkylene radical, at least two carbon atoms of which are in a straight chain; X is —NH— or —O—; m is an integer from 0 to 4; and n is an integer of from 1 to 50.

9. An N-substituted succinimide according to claim 8, wherein $R^1$ is a linear $C_{12}$ or $C_{13}$ radical.

10. An N-substituted succinimide according to claim 9, wherein $R^1$–(OA)$_n$ is polyoxpropylated lauric alcohol, trioxypropylated tridecyl alcohol, tridecyl alcohol with sequential recurrent units of ethylene oxide and propylene oxide or tridecyl alcohol with sequential recurrent units of ethylene oxide and isobutylene oxide.

11. An N-substituted succinimide according to claim 8, wherein the moiety $>$N–(Z—X)$_m$R$^2$ corresponds to a monoprimary amine having the formula $H_2N$—Z–(X)$_m$R$^2$, wherein Z, X, m and $R^2$ are as defined in claim 16, said monoprimary amine being N-oleyl propanediamine, N-isotridecyl propanediamine, 3-isotridecyloxy 1-propylamine, 3-hendecyloxy 1-propylamine, 3-tridecyloxy 1-propylamine or 3-(2-ethyl hexyl)-oxy 1-propylamine.

12. A motor fuel composition, comprising a major proportion of at least one motor fuel and from 10 to 500 ppm by weight of at least one N-substituted succinimide according to claim 16.

13. A motor fuel composition according to claim 12, wherein the proportion of the N-substituted succinimide is from 20 to 200 ppm by weight.

* * * * *